United States Patent
Deimling

(10) Patent No.: US 8,054,076 B2
(45) Date of Patent: Nov. 8, 2011

(54) METHOD AND MAGNETIC RESONANCE SYSTEM TO GENERATE A FAT-REDUCED, SPATIALLY RESOLVED MAGNETIC RESONANCE SPECTRUM

(75) Inventor: Michael Deimling, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 266 days.

(21) Appl. No.: 12/402,651

(22) Filed: Mar. 12, 2009

(65) Prior Publication Data

US 2009/0230960 A1  Sep. 17, 2009

(30) Foreign Application Priority Data

Mar. 13, 2008 (DE) .......................... 10 2008 014 059

(51) Int. Cl.
*G01V 3/00* (2006.01)

(52) U.S. Cl. ....................... 324/307; 324/309

(58) Field of Classification Search .................. 324/307, 324/309

See application file for complete search history.

(56) References Cited

U.S. PATENT DOCUMENTS

| | | | | |
|---|---|---|---|---|
| 5,701,074 | A * | 12/1997 | Zhu | 324/307 |
| 7,170,290 | B2 * | 1/2007 | Miyoshi | 324/309 |
| 7,592,810 | B2 * | 9/2009 | Reeder et al. | 324/309 |

OTHER PUBLICATIONS

"Common Processing of in vivo MR Spectra," 't Zandt, et al, NMR in Biomedicine, 2001, vol. 14, pp. 224-232; Others.

"Removal of Lipid Artifacts in 1H Specztroscopic Imaging by Data Extrapolation," Haupt, et al., Magn.. Reson. Med., vol. 35, 1996, pp. 678-687; Others.

"Comparison of Methods for Reduction of Lipid Contamination for in vivo Proton MR Spectroscopic Imaging of the Brain," Ebel et al, Magn. Reson. Med., vol. 46, 2001, pp. 706-712; Others.

"Comprehensive Processing, Display and Analysis for in vivo MR Spectroscopic Imaging," Maudsley, et al., NMR Biomed. vol. 19, 2006, pp. 492-503; Others.

"MR Spectroscopy Quantitation: A Review of Frequency Domain Methods," Mierisova, et al., NMR Biomed., vol. 14, 2001, pp. 247-259; Others.

"MR Spectroscopy Quantitation: A Review of Time-Domain Methods," Vanhamme, et al. NMR Biomed., vol. 14, 2001, pp. 233-246; Others.

"Spatially Resolved High Resolution Spectroscopy by "four-Dimensional" NMR" Journal of Magnetic Resonance 51, 147-152 (1983).

"Localization of Unaffected Spins in NMR Imaging and Spectroscopy (LOCUS Spectroscopy)"Magnetic Resonance in Medicine 3, pp. 963-969 (1986).

BISTRO: An Outer-Volume Suppression Method That Tolerates RF Field Inhomogeneity Magnetic Resonance in Medicine 45:1095-1102 (2001).

"Pre-Saturation of Irregular Bounded Regions Using Two-Dimensional Waveforms" ISMRM (1999), p. 2079.

* cited by examiner

*Primary Examiner* — Louis Arana

(74) *Attorney, Agent, or Firm* — Schiff Hardin LLP

(57) ABSTRACT

In a method and apparatus for generating a fat-reduced, spatially resolved magnetic resonance spectrum of an examination subject, first measurement data are acquired to generate a spatially resolved spectroscopy measurement, second spatially resolved measurement data are generated that essentially have only fat signal contributions, and the second measurement data are subtracted from the first measurement data to generate the fat-reduced, spatially resolved magnetic resonance spectrum.

17 Claims, 4 Drawing Sheets

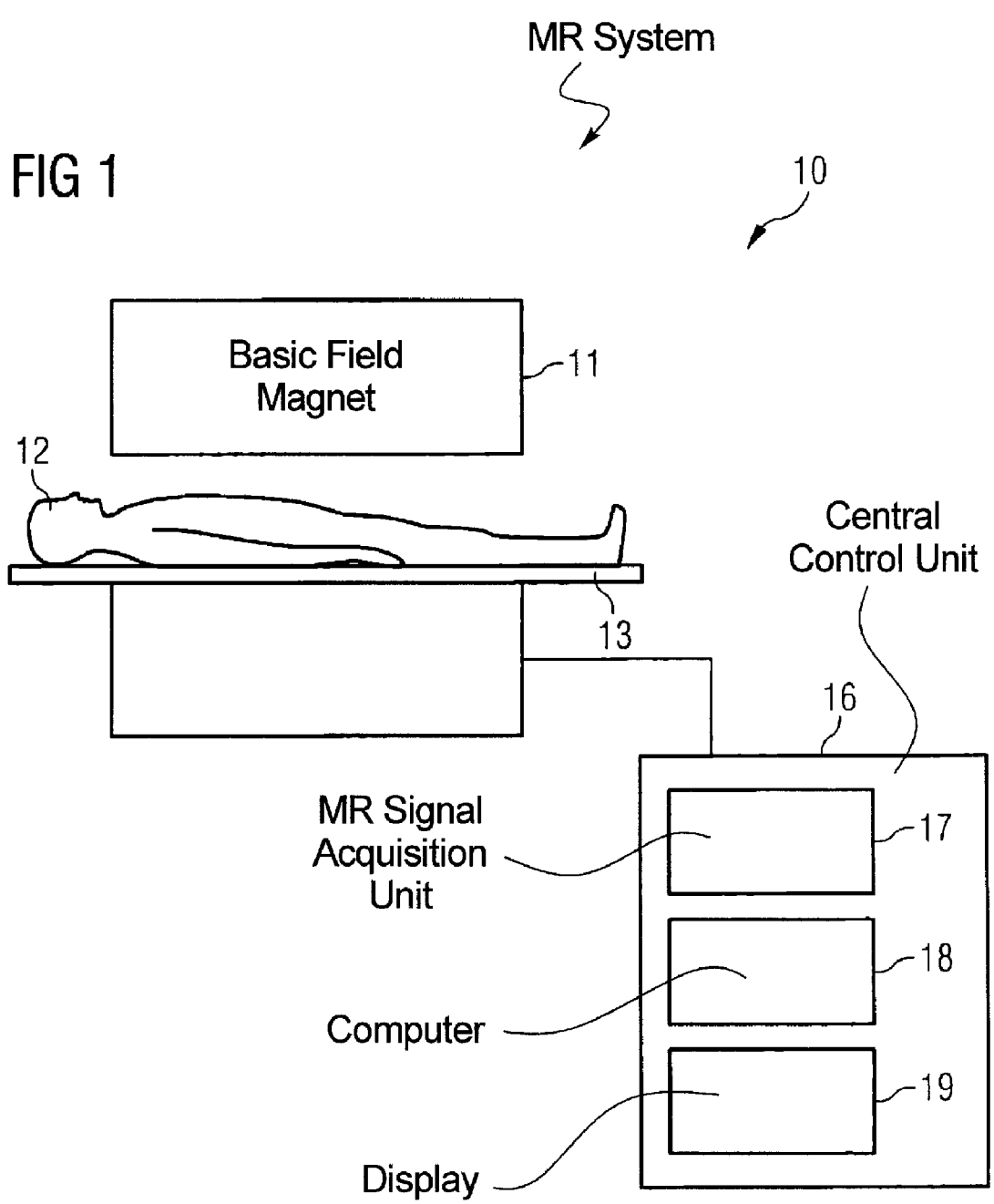

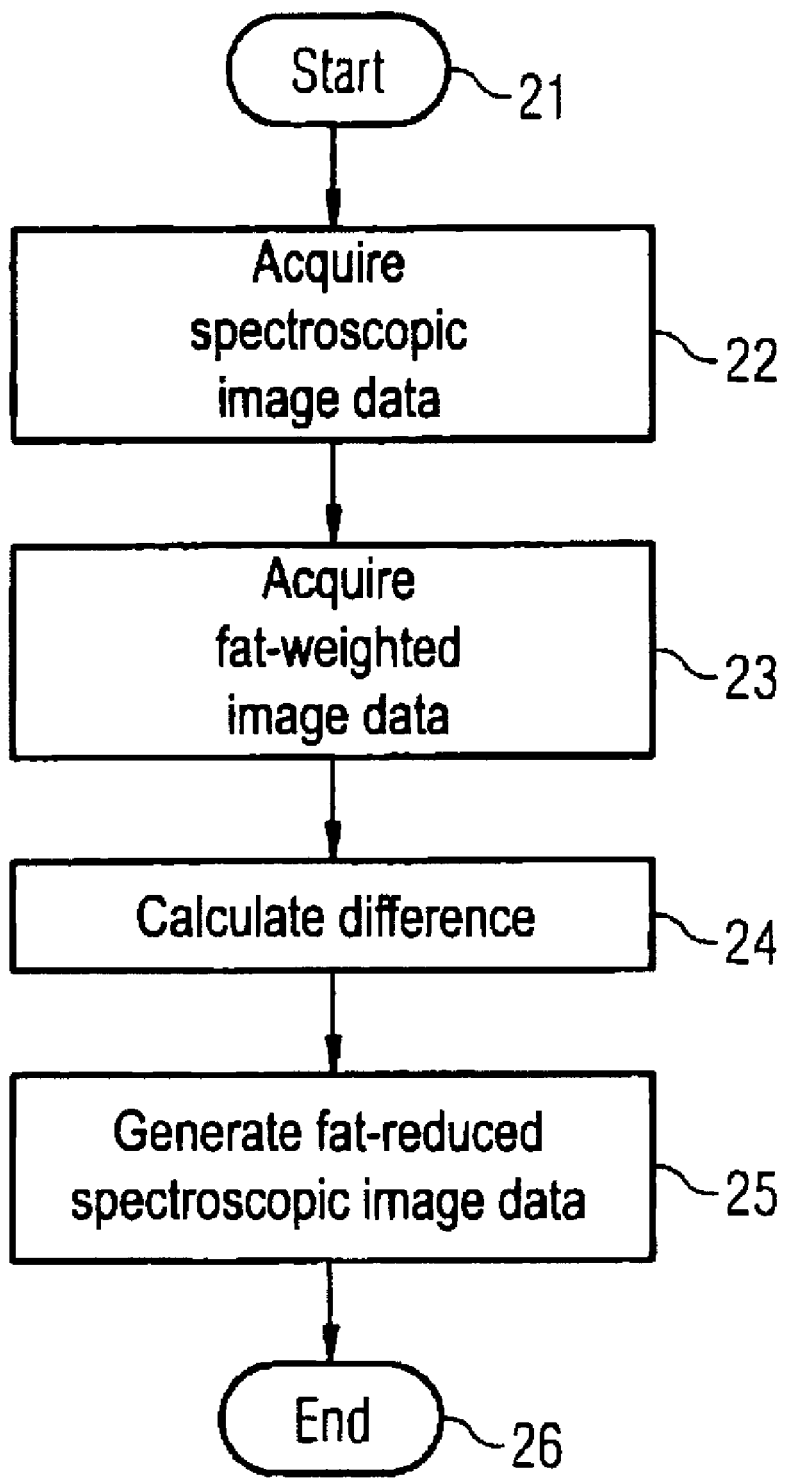

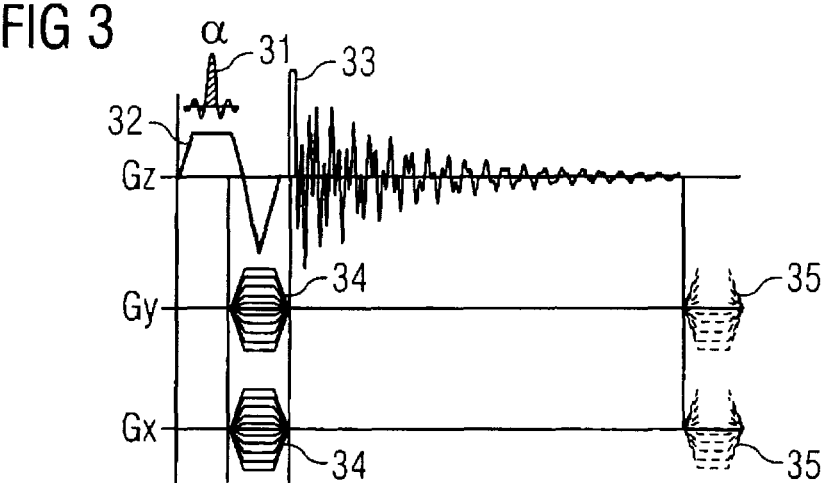
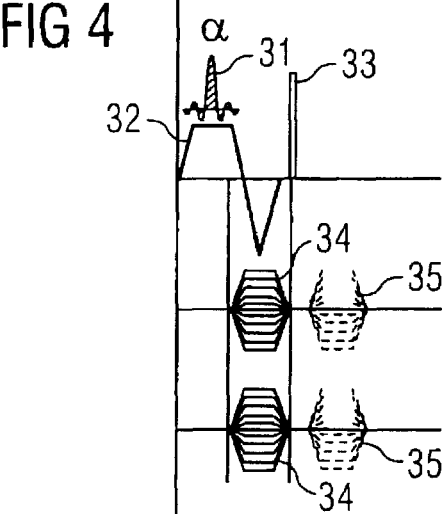
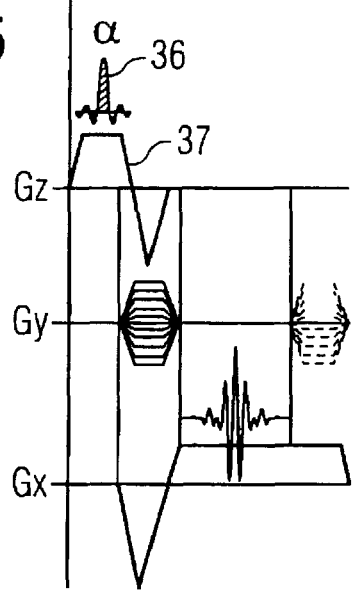

METHOD AND MAGNETIC RESONANCE SYSTEM TO GENERATE A FAT-REDUCED, SPATIALLY RESOLVED MAGNETIC RESONANCE SPECTRUM

BACKGROUND OF THE INVENTION

1. Field of the Invention

The present invention concerns a method to generate a fat-reduced, spatially resolved magnetic resonance spectrum of an examination subject and a magnetic resonance system for implementing such a method.

2. Description of the Prior Art

The modality of spatially resolved MR spectroscopy differs from the modality of MR imaging in that, in addition to the spatial resolution of the MR signals, the chemical shift should also be spatially resolved in spectroscopy. ("Spatial resolution" and "spatially resolved" mean assigning values to the signal in question for associated positions in space.) In general, spectroscopic MR methods must in particular account for the circumstances that the metabolic products of interest exhibit a concentration that is approximately four orders of magnitude lower than the water and fat molecules shown in MR imaging. The significant information of spatially resolved MR spectroscopy lies in the spectral range between the line of free water at 0 ppm and the lines of the fat protons at approximately 3 ppm. For example, these lipid signals appear outside of the examined region or VOI (volume of interest) in the brain spectrum of the region and make the interpretation and quantification of the lines of metabolites (such as NAA, choline, GABA and inositol) more difficult. The method designated as the CSI (Chemical Shift Imaging) method is known in spectroscopic imaging. In CSI mammo-spectroscopies, as well as in prostate spectroscopies, the determination of the citrate/choline/creatine ratio can be very strongly distorted by the contamination of the dominating fat spectrum, assuming it is not made impossible in the first place.

In the prior art it is known to suppress the contribution of the fat spectrum by the application of pulses that excite the fat signals outside of the examined range and destroy their magnetization, so that these fat signals make no or only a slight signal contribution in the subsequent imaging spectroscopy. However, in many applications these saturation bands that are to be spatially placed can only be insufficiently adapted to the anatomy. The magnetization of the signal is additionally restored again in part by the refocusing effect of the many pulses on the magnetization in the overlap range of the saturation pulses, so artifacts can arise. Furthermore, the placement of the many different saturation bands to define the saturated regions is time-consuming.

SUMMARY OF THE INVENTION

An object of the present invention is to provide a method wherein the fat signal contributions in a spectroscopy signal in spectroscopic imaging are suppressed in a simple manner.

This object is achieved in accordance with the invention by a method to generate the fat-reduced, spatially resolved magnetic resonance spectrum, in which first measurement data are acquired to generate a spatially resolved spectroscopy measurement. In an additional step, second spatially resolved measurement data are generated that essentially have only fat signal contributions. The second measurement data are subtracted from the first measurement data in order to generate the fat-reduced, spatially resolved magnetic resonance spectrum. The spatial resolution of the first measurement data is advantageously essentially equal to the spatial resolution of the second measurement data. Fat signals are typically shown spatially offset in the image due to the different resonance frequency. However, since the offset of the fat signals in the spatially resolved spectroscopy measurement is equal to the offset of the fat signals in the second spatially resolved measurement data, a fat-reduced spectroscopy measurement can be achieved by subtraction of the second spatially resolved measurement data (known as the lipid image).

In an embodiment of the invention, the first measurement data are acquired with the CSI method. In the CSI method, the acquisitions of spectra of many spatial target volumes are enabled simultaneously, wherein in the CSI method the volume from which the spectrum is to be presented is freely selectable after the measurement. One possibility to generate the second spatially resolved measurement data is to likewise acquire these measurement data with the CSI method. While the repetition time TR is optimally long in the acquisition of the first measurement data according to the CSI method, it is optimally short in the acquisition of the second spatially resolved measurement data in order to achieve a fat weighting of the generated measurement data.

In addition to the possibility of likewise acquiring the second spatially resolved measurement data with a spectroscopy measurement, the possibility also exists to generate the second measurement data by the acquisition of normal (i.e. non-spectroscopic) fat-weighted imaging sequences. In order to simplify a subtraction, however, the spatial resolution of the second measurement data should always be equal to the spatial resolution of the first measurement data.

Either the fat-weighting of the imaging sequence can be achieved via suitable selection of the image parameters, or it is possible to acquire the second measurement data such that second measurement signals are acquired and converted into MR data sets, wherein the non-fat signal portions in the MR image data are suppressed, for example via segmentation of the MR image data to detect the brightest [lightest] fat signals in the image and via suppression of the non-fat signals in said image. Naturally, the two possibilities can be combined.

If the second measurement data are generated with the use of a spectroscopic imaging sequence, a strongly $T_1$-weighted CSI measurement sequence can be used, for example. Since the repetition time is kept optimally short, only very few measurement points are acquired per phase coding step. In principle, one measurement point per phase coding step is sufficient; however, multiple measurement points (for example up to 5 or 10 measurement points per phase coding step) can also be acquired.

In the event that the second measurement data are generated by a non-spectroscopic, conventional imaging sequence, the selection of a strongly $T_1$-weighted imaging sequence is possible, for example, from which the measurement signals of an STIR (Short Tau Inversion Recovery) imaging sequence are subtracted. A pure fat image is thereby obtained. An additional possibility exists in the acquisition of a strongly $T_1$-weighted spin echo sequence with short repetition time and a flip angle $\alpha<90°$.

The fat signal portions in the second spatially resolved measurement data can also be intensified by, for example, in the conversion of the signal portions into grayscale values, the fat portions with a high signal are more strongly intensified than the remaining signal portions with a lower signal. This means that the conversion of the measurement data generated with the use of a fat-weighted imaging sequence are non-linearly converted into grayscale values in order to more strongly emphasize the fat signal portions. After such a non-linear correction, the fat-amplified image can again be Fourier-transformed, and the resulting complex raw data represent the second measurement data that can then be subtracted from the first measurement data.

In general, the subtraction of the second measurement data from the first measurement data is possible in image space (image domain) or in the raw data/Fourier space (spatial domain).

For example, a repetition time between 60 and 200 ms (advantageously between 80 and 120 ms, and more advantageously of 100 ms) is conceivable to generate a fat weighting of the second spatially resolved measurement data.

The above object also is achieved in accordance with the present invention by a magnetic resonance system that generate a fat-reduced, spatially resolved magnetic resonance spectrum as described above, by executing the method described above, including all embodiments thereof.

The above object also is achieved in accordance with the present invention by a computer-readable medium encoded with programming instructions which, when the computer-readable medium is loaded into a controller of a magnetic resonance system, cause the magnetic resonance system to implement the method described above, including all embodiments thereof.

BRIEF DESCRIPTION OF THE DRAWINGS

FIG. 1 schematically illustrates a magnetic resonance system to generate a fat-reduced, spatially resolved MR spectrum.

FIG. 2 is a flowchart for generation of a fat-reduced, spatially resolved MR spectrum.

FIG. 3 is an exemplary spectroscopic imaging sequence to generate the first measurement data.

FIG. 4 is a schematically illustrated sequence diagram to generate the second measurement data via fat-weighted, spatially resolved MR spectra.

FIG. 5 is a schematically illustrated imaging sequence to generate fat-weighted imaging data to generate the second measurement data.

DESCRIPTION OF THE PREFERRED EMBODIMENTS

Figure 6:
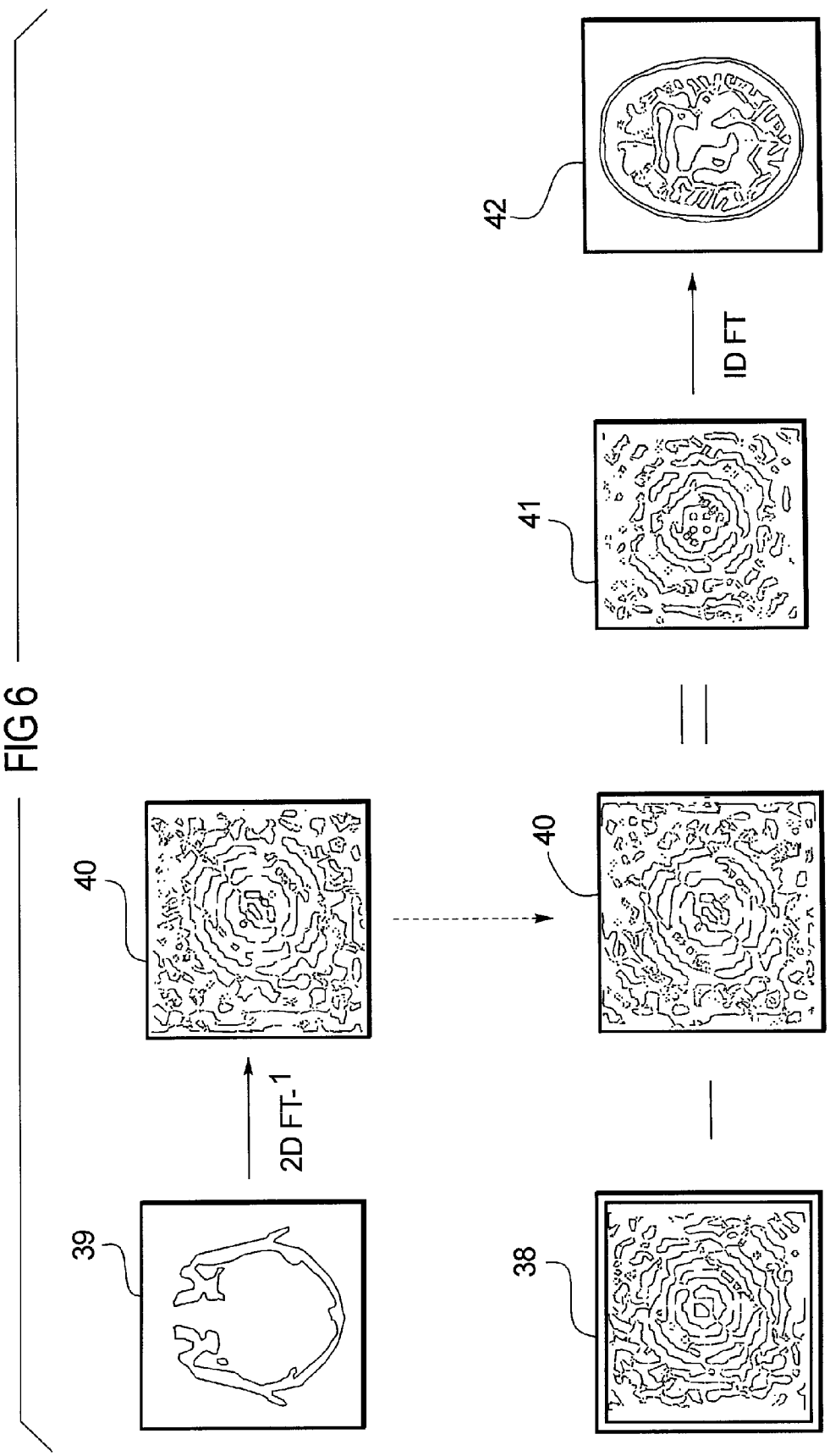
FIG. 6 schematically illustrate the generation of fat-reduced, spatially resolved MR spectra using image data (raw data).

An MR system 10 is schematically shown in FIG. 1, having a basic field magnet 11 to generate a polarization field B0. An examination subject (person) 12 is arranged on a bed 13 in the MR system 10. The magnetization generated in the examination subject can be excited by an RF arrangement (not shown), wherein spatially resolved MR spectra can be acquired by simultaneous switching of gradients.

The type and manner of how a spectroscopic MR image is generated in an MR system via radiation of a sequence of RF pulses and gradients is known in general to those skilled in the art, such that a precise explanation of this is foregone for reasons of clarity. The MR system 10 is controlled by an operator via a central control unit 16. This central control unit possesses an MR signal acquisition unit 17 that controls the switching of the RF pulses and gradients. Furthermore, a computer 18 is provided which subtracts the generated second measurement data from first measurement data in order to obtain a fat-reduced, spatially resolved MR spectrum. The spectroscopic image data can be displayed on a display 19.

How the fat-reduced, spatially resolved spectroscopy data are acquired is explained in detail in connection with FIGS. 2-6. The basic steps which are necessary to generate the fat-reduced spectroscopy signal are presented in FIG. 2. After a start of the method in Step 21, spectroscopic image data are acquired in Step 22. The imaging sequence used to generate these spectroscopic image data is schematically presented in FIG. 3. The spectroscopic imaging shown in FIG. 3 is a 2D CSI imaging sequence in which a transversal magnetization 33 that decays exponentially is generated via radiation of an RF pulse α 31 with simultaneous switching of a slice selection gradient 32. The two phase coding gradients 34 are switched in the phase coding direction $G_y$ and readout direction $G_x$. 32×32 pixels can be used as a spatial resolution, for example; however, other spatial resolutions are also possible. The signal readout respectively ensues between the phase coding gradients 34 and 35. The signals acquired by the imaging sequence from FIG. 3 contain fat and water portions.

As can be seen in FIG. 2, fat-weighted image data are acquired in Step 23. These fat-weighted image data can be acquired in various ways. One possibility is shown as an example in FIG. 4. The imaging sequence shown in FIG. 4 corresponds to the spectroscopic imaging sequence presented in FIG. 3, wherein a short repetition time between the two phase coding gradients 34 and 35 is selected (in contrast to the imaging sequence from FIG. 3). The very short repetition time TR leads to a strong fat weighting of the acquired signals. In principle, one measurement point per phase coding step is sufficient; however, multiple measurement points are naturally also possible. The second measurement data generated with the imaging sequence from FIG. 4 are subtracted from the first measurement data that were generated with the imaging sequence from FIG. 3. This Step 24 in FIG. 2 leads to fat-reduced measurement data that can be used in Step 25 to generate fat-reduced spectroscopic image data. The method ends in Step 26.

Instead of the spectroscopic imaging sequence shown in FIG. 4 for generation of the second measurement data, these can also be generated with a non-spectroscopic imaging sequence as shown in FIG. 5. What is known as a flip image can be generated using a very short repetition time by radiation of an α pulse 36 during the switching of a slice selection gradient 37 and by switching phase coding gradients as well as the signal readout during a readout gradient. The spatial resolution of this lipid image should be identical to the spatial resolution of the spectroscopic imaging sequence shown in FIG. 3. For example, this lipid image can be generated with a strongly $T_1$-weighted spin echo sequence or a strongly $T_1$-weighted spin echo sequence from which what is known as a STIR image is subtracted. It is likewise possible to achieve the lipid image via spectral saturation of the water signals, or the 2-point Dixon method can be resorted to in which the fat signal and the water signal are either added to or subtracted from one another, depending on the echo time.

The measurement signals detected in the generation of the lipid image can be post-processed via additional steps in order to further intensify the fat signal portion in the image. Since the fat signal portions in the image typically have a greater signal intensity than the remaining signal portions, it is possible via segmentation algorithms to isolate the lipid signals and to suppress the other signal portions in the image. Such a segmented lipid image can subsequently be transformed back again into raw data space, whereby the second measurement data are generated that are subtracted from the first measurement data.

An additional possibility to intensify the fat signal is the use of a non-line characteristic line in the conversion of second spatially resolved measurement data (for the lipid image) into grayscale values. By using a non-linear (for example quadratic) characteristic line, the fat signal portions with high signal values can be additionally intensified relative to the other signal portions.

The method according to the invention is explained again in detail in FIG. 6 using MR images. The raw data 38 are first measurement data containing fat and water, which first measurement data are presented in raw data space from which spatially resolved spectroscopy images can be generated (namely, the first measurement data. Furthermore, a lipid image 39 is generated (for example via an imaging sequence as shown in FIG. 5) which possesses essentially only the fat signal portions. This lipid image 39 can have been generated via post-processing of the actual measurement signals, for example as previously mentioned via segmentation and/or use of a non-linear characteristic line. The second measurement data 40 which represent the corrected raw data can be generated from the lipid image 39 via inverse Fourier transformation. These corrected raw data are subtracted from the raw data 38, whereby fat-reduced raw data 41 are generated that can in turn be converted via Fourier transformation into a spatially resolved, fat-reduced magnetic resonance spectrum 42.

With the method described above it is possible according to the invention to reduce the fat signal portion in spectroscopy imaging. The necessary and described processing steps can be automated, whereby fat-reduced spectra can be generated automatically. The method according to the invention furthermore has the advantage that no saturation bands must be used, such that magnetizations induced by saturation bands cannot occur, whereby artifacts can be prevented. The anatomical image field in which spectra can be presented is not limited. The described fat saturation method is particularly advantageous in the examination of regions in which fat lies in close spatial proximity to aqueous tissue, for example in prostate or mammo-spectroscopy.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating a fat-reduced, spatially resolved magnetic resonance spectrum of an examination subject, comprising the steps of:
   acquiring first magnetic resonance measurement data from an examination subject that include contributions originating from fat tissue in the examination subject and contributions originating from non-fat tissue in the examination subject, and generating spatially resolved spectroscopic data therefrom, having a spatial resolution;
   acquiring second magnetic resonance measurement data from the examination subject that include only contributions from said fat tissue in said examination subject, and generating spatially resolved measurement data therefrom having a spatial resolution substantially equal to the spatial resolution of said spatially resolved spectroscopic data; and
   subtracting said spatially resolved measurement data from said spatially resolved spectroscopic data to obtain a fat-reduced, spatially resolved magnetic resonance spectrum.

2. A method as claimed in claim 1 comprising acquiring said first magnetic resonance measurement data by chemical shift magnetic resonance imaging.

3. A method as claimed in claim 1 comprising acquiring said second magnetic resonance measurement data by chemical shift magnetic resonance imaging.

4. A method as claimed in claim 1 comprising acquiring said second magnetic resonance measurement data with a fat-weighted imaging sequence.

5. A method as claimed in claim 4 comprising acquiring said second magnetic resonance measurement data by:
   acquiring magnetic resonance signals from the examination subject;
   converting said magnetic resonance signals into said second magnetic resonance image data in a conversion procedure; and
   in said conversion procedure, suppressing signal contributions from said non-fat tissue of said examination subject.

6. A method as claimed in claim 5 comprising identifying signal contributions from fat tissue in said magnetic resonance image data by segmentation of said magnetic resonance image data.

7. A method as claimed in claim 1 comprising acquiring said second magnetic resonance measurement data by acquiring magnetic resonance signals from the examination subject that contain signal contributions originating substantially only from said fat tissue in the examination subject.

8. A method as claimed in claim 7 comprising acquiring said magnetic resonance signals with a spectroscopic $T_1$-weighted CSI magnetic resonance sequence.

9. A method as claimed in claim 8 wherein said spectroscopic $T_1$-weighted CSI sequence comprises multiple phase coding steps, and acquiring no more than 5 measurement points in each of said phase coding steps.

10. A method as claimed in claim 1 comprising acquiring said second magnetic resonance measurement data with a $T_1$ weighted imaging sequence and subtracting therefrom measurement signals from a Short Tau Inversion Recovery magnetic resonance imaging sequence.

11. A method as claimed in claim 1 comprising acquiring said second magnetic resonance data by acquiring magnetic resonance signals from the examination subject in which contributions from fat tissue in the examination subject have a higher signal intensity than a remainder of signal contributions, and non-linearly converting the signal intensity of said magnetic resonance signals into greyscale values in a conversion procedure wherein said signal contributions from said fat tissue are more strongly increased than said remainder of signal contributions.

12. A method as claimed in claim 11 wherein said conversion procedure produces non-linearly converted greyscale values, and wherein said method comprises transforming said non-linearly converted greyscale values back into raw data space to form said spatially resolved measurement data that are subtracted from said spatially resolved spectroscopic data.

13. A method as claimed in claim 1 comprising acquiring said second magnetic resonance measurement data using a magnetic resonance sequence having a short repetition time between 40 and 200 ms.

14. A method as claimed in claim 1 comprising acquiring said second magnetic resonance measurement data using a magnetic resonance sequence having a short repetition time between 80 and 120 ms.

15. A method as claimed in claim 1 comprising acquiring said second magnetic resonance measurement data with a magnetic resonance imaging sequence having a short repetition time of approximately 100 ms.

16. A magnetic resonance system comprising:
a magnetic resonance data acquisition unit that acquires first magnetic resonance data from an examination subject, that include contributions from fat tissue in the examination subject and non-fat tissue in the examination subject and that generates spatially resolved spectroscopic data therefrom having a spatial resolution, and that acquires second magnetic resonance data from the examination subject, having substantially only contributions originating from said fat tissue in the examination subject and that generates spatially resolved measurement data therefrom, having a spatial resolution substantially equal to the spatial resolution of said spatially resolved spectroscopic data; and
a computer supplied with said first and second magnetic resonance measurement data, said computer being configured to subtract said second magnetic resonance measurement data from said first magnetic resonance measurement data to obtain a fat-reduced, spatially resolved magnetic resonance spectrum.

17. A non-transitory computer-readable storage medium encoded with programming instructions, said medium being loadable into a computer that operates a magnetic resonance system, said programming instructions causing said computer to:
operate said magnetic resonance system to acquire first magnetic resonance measurement data from an examination subject that include contributions originating from fat tissue in the examination subject and contributions originating from non-fat tissue in the examination subject, and to generate spatially resolved spectroscopic data therefrom, having a spatial resolution;
operate said magnetic resonance system to acquire second magnetic resonance measurement data from the examination subject that include only contributions from said fat tissue in said examination subject, and to generate spatially resolved measurement data therefrom, having a spatial resolution substantially equal to the spatial resolution of said spatially resolved spectroscopic data; and
subtract said spatially resolved measurement data from said spatially resolved spectroscopic data to obtain a fat-reduced, spatially resolved magnetic resonance spectrum.

* * * * *